(12) United States Patent
Östman et al.

(10) Patent No.: US 7,632,095 B2
(45) Date of Patent: Dec. 15, 2009

(54) METHOD FOR FORMING A DENTAL PROSTHESIS

(75) Inventors: Pär-Olov Östman, Falun (SE); Theodore M. Powell, Palm Beach Gardens, FL (US)

(73) Assignee: Biomet 3I, Inc., Palm Beach Gardens, FL (US)

( * ) Notice: Subject to any disclaimer, the term of this patent is extended or adjusted under 35 U.S.C. 154(b) by 100 days.

(21) Appl. No.: 11/891,817

(22) Filed: Aug. 13, 2007

(65) Prior Publication Data
US 2009/0047630 A1 Feb. 19, 2009

(51) Int. Cl.
*A61C 13/12* (2006.01)

(52) U.S. Cl. .................. 433/172; 433/72; 433/173; 433/218

(58) Field of Classification Search .............. 433/172, 433/174, 175, 176, 218, 223, 173, 72
See application file for complete search history.

(56) References Cited

U.S. PATENT DOCUMENTS

| | | | |
|---|---|---|---|
| 3,304,608 A | 2/1967 | Frohnecke | |
| 3,958,471 A | 5/1976 | Willer | 82/1 C |
| 4,011,602 A | 3/1977 | Rybicki et al. | 3/1.9 |
| 4,086,701 A | 5/1978 | Kawahara et al. | 32/10 A |
| 4,177,562 A | 12/1979 | Miller et al. | 433/174 |
| 4,253,833 A | 3/1981 | Edelman | 433/173 |
| 4,306,862 A | 12/1981 | Knox | 433/77 |
| 4,341,312 A | 7/1982 | Scholer | 211/60 T |
| 4,483,675 A | 11/1984 | Marshall | 433/141 |
| 4,547,157 A | 10/1985 | Driskell | 433/173 |
| 4,575,340 A | 3/1986 | Lustig | 433/173 |
| 4,624,673 A | 11/1986 | Meyer | 623/16 |
| 4,681,542 A | 7/1987 | Baum | |
| 4,708,654 A | 11/1987 | Branemark | 433/213 |
| 4,713,003 A | 12/1987 | Symington et al. | 433/173 |
| 4,713,004 A | 12/1987 | Linkow et al. | 433/174 |
| 4,722,688 A | 2/1988 | Lonca | 433/173 |
| 4,738,623 A | 4/1988 | Driskell | 433/173 |
| 4,744,753 A | 5/1988 | Ross | 433/173 |
| D296,362 S | 6/1988 | Branemark | D24/33 |
| 4,758,161 A | 7/1988 | Niznick | 433/173 |
| 4,763,788 A | 8/1988 | Jorneus et al. | 206/438 |
| 4,767,331 A | 8/1988 | Hoe | 433/213 |

(Continued)

FOREIGN PATENT DOCUMENTS

CH 679117 A5 12/1991

(Continued)

*Primary Examiner*—Cris L Rodriguez
*Assistant Examiner*—Eric Rosen
(74) *Attorney, Agent, or Firm*—Nixon Peabody LLP

(57) ABSTRACT

A method of creating a provisional dental prosthesis on an implant placed in bone retains a conical abutment to the implant. A first intermediate component secures to the conical abutment. A second intermediate component attaches to the first intermediate component. The second intermediate component comprises a polymeric material. A prosthetic template is placed over the second intermediate component. The prosthetic template is filled with a hardenable material. After the prosthetic template is filled, the process removes the prosthetic template with the second intermediate component within the hardenable material. A provisional prosthesis forms from the hardenable material, the provisional prosthesis contains the second intermediate component. The provisional prosthesis connect to the first intermediate component by affixing the second intermediate component to the first intermediate component.

30 Claims, 9 Drawing Sheets

U.S. PATENT DOCUMENTS

| | | | |
|---|---|---|---|
| 4,772,204 A | 9/1988 | Söderberg | 433/174 |
| 4,826,434 A | 5/1989 | Krueger | 433/174 |
| 4,842,518 A | 6/1989 | Linkow et al. | 433/174 |
| 4,850,870 A | 7/1989 | Lazzara et al. | 433/174 |
| 4,850,873 A | 7/1989 | Lazzara et al. | 433/220 |
| 4,856,994 A | 8/1989 | Lazzara et al. | 433/173 |
| 4,872,839 A | 10/1989 | Brajnovic | 433/173 |
| 4,955,811 A | 9/1990 | Lazzara et al. | 433/173 |
| 4,960,381 A | 10/1990 | Niznick | 433/174 |
| 4,988,297 A | 1/1991 | Lazzara et al. | 433/173 |
| 4,988,298 A | 1/1991 | Lazzara et al. | 433/173 |
| 4,995,810 A | 2/1991 | Soderberg | 433/141 |
| 5,000,685 A | 3/1991 | Brajnovic | 433/173 |
| 5,006,069 A | 4/1991 | Lazzara et al. | 433/173 |
| 5,015,186 A | 5/1991 | Detsch | 433/173 |
| 5,022,860 A | 6/1991 | Lazzara et al. | 433/174 |
| 5,026,280 A * | 6/1991 | Durr et al. | 433/175 |
| 5,026,285 A | 6/1991 | Durr et al. | 433/173 |
| 5,030,096 A | 7/1991 | Hurson et al. | 433/173 |
| 5,035,619 A | 7/1991 | Daftary | 433/173 |
| 5,040,983 A | 8/1991 | Binon | 433/173 |
| 5,055,047 A | 10/1991 | Names | 433/214 |
| 5,061,181 A | 10/1991 | Niznick | 433/174 |
| 5,062,800 A | 11/1991 | Niznick | 433/229 |
| 5,071,351 A | 12/1991 | Green, Jr. et al. | 433/173 |
| 5,073,111 A | 12/1991 | Daftary | 433/173 |
| 5,100,323 A | 3/1992 | Friedman et al. | 433/173 |
| 5,104,318 A | 4/1992 | Piche et al. | 433/174 |
| 5,106,300 A | 4/1992 | Voitik | 433/173 |
| 5,116,225 A | 5/1992 | Riera | 433/173 |
| 5,122,059 A | 6/1992 | Dürr et al. | 433/173 |
| 5,125,839 A | 6/1992 | Ingber et al. | 433/169 |
| 5,125,841 A | 6/1992 | Carlsson et al. | 433/213 |
| 5,135,395 A | 8/1992 | Marlin | 433/174 |
| 5,145,371 A | 9/1992 | Jörnéus | 433/173 |
| 5,145,372 A | 9/1992 | Daftary et al. | 433/173 |
| 5,145,612 A | 9/1992 | Reay et al. | 261/79.2 |
| 5,154,612 A | 10/1992 | Carlsson et al. | 433/173 |
| 5,174,755 A | 12/1992 | Fukuda | 433/173 |
| 5,188,800 A | 2/1993 | Green, Jr. et al. | 422/23 |
| 5,195,891 A | 3/1993 | Sulc | 433/173 |
| 5,195,892 A | 3/1993 | Gersberg | 433/174 |
| 5,199,873 A | 4/1993 | Schulte et al. | 433/174 |
| 5,205,745 A | 4/1993 | Kamiya et al. | 433/173 |
| 5,209,659 A | 5/1993 | Friedman et al. | 433/173 |
| 5,209,666 A | 5/1993 | Balfour et al. | 433/173 |
| 5,213,498 A | 5/1993 | Pelerin | 433/37 |
| 5,213,502 A | 5/1993 | Daftary | 433/172 |
| 5,246,370 A | 9/1993 | Coatoam | 433/173 |
| 5,259,759 A | 11/1993 | Jorneus et al. | 433/173 |
| 5,281,140 A | 1/1994 | Niznick | 433/172 |
| 5,286,195 A | 2/1994 | Clostermann | 433/172 |
| 5,292,252 A | 3/1994 | Nickerson et al. | 433/173 |
| 5,297,963 A | 3/1994 | Dafatry | 433/172 |
| 5,302,125 A | 4/1994 | Kownacki et al. | 433/173 |
| 5,316,476 A | 5/1994 | Krauser | 433/173 |
| 5,316,477 A | 5/1994 | Calderon | 433/173 |
| 5,322,443 A | 6/1994 | Beaty | 433/141 |
| 5,328,371 A | 7/1994 | Hund et al. | 433/173 |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,344,457 A | 9/1994 | Pilliar et al. | 623/16 |
| 5,350,297 A * | 9/1994 | Cohen | 433/76 |
| 5,350,302 A | 9/1994 | Marlin | 433/174 |
| 5,362,234 A | 11/1994 | Salazar et al. | 433/169 |
| 5,362,235 A | 11/1994 | Daftary | 433/172 |
| 5,362,237 A | 11/1994 | Chalifoux | 433/220 |
| 5,368,483 A | 11/1994 | Sutter et al. | 433/173 |
| 5,376,004 A | 12/1994 | Mena | 433/173 |
| 5,399,090 A | 3/1995 | Padros-Fradera | 433/173 |
| 5,417,570 A | 5/1995 | Zuest et al. | 433/177 |
| 5,419,702 A | 5/1995 | Beaty et al. | 433/214 |
| 5,431,567 A | 7/1995 | Daftary | 433/172 |
| 5,433,606 A | 7/1995 | Niznick et al. | 433/173 |
| 5,437,550 A | 8/1995 | Beaty et al. | 433/141 |
| 5,437,551 A | 8/1995 | Chalifoux | 433/173 |
| 5,458,488 A | 10/1995 | Chalifoux | 433/173 |
| 5,476,382 A | 12/1995 | Daftary | 433/172 |
| 5,476,383 A | 12/1995 | Beaty et al. | 433/214 |
| 5,478,237 A | 12/1995 | Ishizawa | 433/201.1 |
| 5,489,210 A | 2/1996 | Hanosh | 433/173 |
| 5,492,471 A | 2/1996 | Singer | 433/172 |
| 5,503,558 A | 4/1996 | Clokie | 433/173 |
| 5,533,898 A | 7/1996 | Mena | 433/173 |
| 5,538,426 A | 7/1996 | Harding et al. | 433/172 |
| 5,547,377 A | 8/1996 | Daftary | 433/172 |
| 5,556,280 A | 9/1996 | Pelak | |
| 5,564,921 A | 10/1996 | Marlin | 433/172 |
| 5,564,923 A | 10/1996 | Grassi et al. | 433/173 |
| 5,564,924 A | 10/1996 | Kwan | 433/173 |
| 5,573,401 A | 11/1996 | Davidson et al. | 433/201.1 |
| 5,588,838 A | 12/1996 | Hansson et al. | 433/173 |
| 5,636,989 A | 6/1997 | Somborac et al. | 433/173 |
| 5,639,237 A | 6/1997 | Fontenot | 433/173 |
| 5,642,996 A | 7/1997 | Mochida et al. | 433/174 |
| 5,651,675 A | 7/1997 | Singer | 433/172 |
| 5,662,475 A | 9/1997 | Mena | 433/172 |
| 5,662,476 A | 9/1997 | Ingber et al. | 433/213 |
| 5,674,069 A | 10/1997 | Osorio | 433/172 |
| 5,674,071 A | 10/1997 | Beaty et al. | 433/172 |
| 5,674,073 A | 10/1997 | Ingber et al. | 433/213 |
| 5,683,249 A | 11/1997 | Ibsen et al. | 433/201.1 |
| 5,685,715 A | 11/1997 | Beaty et al. | 433/173 |
| 5,688,123 A | 11/1997 | Meiers et al. | 433/173 |
| 5,695,336 A | 12/1997 | Lazzara et al. | 433/173 |
| 5,702,346 A | 12/1997 | Lazzara et al. | 433/173 |
| 5,709,547 A | 1/1998 | Lazzara et al. | 433/174 |
| 5,725,375 A | 3/1998 | Rogers | 433/172 |
| 5,727,943 A | 3/1998 | Beaty et al. | 433/174 |
| 5,733,124 A | 3/1998 | Kwan | 433/173 |
| 5,749,732 A | 5/1998 | Sendax | 433/174 |
| 5,752,830 A | 5/1998 | Suarez | 433/173 |
| 5,759,034 A | 6/1998 | Daftary | 433/173 |
| 5,762,500 A | 6/1998 | Lazarof | 433/213 |
| 5,779,480 A | 7/1998 | Groll et al. | 433/173 |
| 5,782,637 A | 7/1998 | Cosenza | 433/173 |
| 5,782,918 A | 7/1998 | Klardie et al. | 623/16 |
| 5,788,494 A | 8/1998 | Phimmasone | 433/213 |
| 5,816,809 A | 10/1998 | Sapkos | 433/172 |
| 5,823,777 A | 10/1998 | Misch et al. | 433/174 |
| 5,829,977 A | 11/1998 | Rogers et al. | 433/172 |
| 5,829,981 A | 11/1998 | Ziegler | 433/214 |
| 5,842,864 A | 12/1998 | Unger | 433/172 |
| 5,846,079 A | 12/1998 | Knode | 433/213 |
| 5,868,572 A | 2/1999 | Lazzara et al. | 433/173 |
| 5,873,722 A | 2/1999 | Lazzara et al. | 433/173 |
| 5,873,727 A | 2/1999 | Barlow | 434/128 |
| 5,879,161 A | 3/1999 | Lazzara | 433/173 |
| 5,899,695 A | 5/1999 | Lazzara et al. | 433/173 |
| 5,899,697 A | 5/1999 | Lazzara et al. | 433/173 |
| 5,904,483 A | 5/1999 | Wade | 433/173 |
| 5,906,489 A | 5/1999 | Khazzam et al. | |
| 5,927,979 A | 7/1999 | Misch et al. | 433/173 |
| 5,934,906 A | 8/1999 | Phimmasone | 433/172 |
| 5,938,443 A | 8/1999 | Lazzara et al. | 433/173 |
| 5,944,525 A | 8/1999 | Ura | 433/173 |
| 5,947,736 A | 9/1999 | Behrend | 433/214 |
| 5,964,591 A | 10/1999 | Beaty et al. | 433/173 |
| 6,030,219 A | 2/2000 | Zuest et al. | |
| 6,068,478 A | 5/2000 | Grande et al. | 433/172 |
| 6,068,480 A | 5/2000 | Misch et al. | 433/173 |
| 6,083,004 A | 7/2000 | Misch et al. | 433/173 |
| 6,120,293 A | 9/2000 | Lazzara et al. | 433/173 |

| | | | | | | | |
|---|---|---|---|---|---|---|---|
| 6,142,782 | A | 11/2000 | Lazarof .................. 433/174 | DE | 40 28 855 A1 | 3/1992 | |
| 6,149,433 | A | 11/2000 | Ziegler et al. ............ 433/214 | DE | 19 742 381 | 2/1999 | |
| 6,155,828 | A | 12/2000 | Lazzara et al. ............ 433/173 | EP | 0 190 670 A2 | 8/1986 | |
| 6,159,010 | A | 12/2000 | Rogers et al. ............ 433/172 | EP | 0 442 855 A1 | 8/1991 | |
| 6,217,331 | B1 | 4/2001 | Rogers et al. ............ 433/173 | EP | 0 473 262 | 3/1992 | |
| 6,227,856 | B1 | 5/2001 | Beaty et al. ............... 433/172 | EP | 0 657 146 A1 | 6/1995 | |
| 6,247,932 | B1 | 6/2001 | Sutter ...................... 433/173 | EP | 0 727 193 A1 | 8/1996 | |
| 6,276,938 | B1 | 8/2001 | Jorneus et al. ............ 433/172 | EP | 0 814 724 B1 | 1/1998 | |
| 6,280,195 | B1 | 8/2001 | Broberg et al. | EP | 0 879 025 B1 | 11/1998 | |
| 6,299,447 | B1 | 10/2001 | Zuest et al. | FR | 1 463 860 | 7/1965 | |
| 6,325,628 | B1 | 12/2001 | Morgan | GB | 1 291 470 | 10/1972 | |
| 6,332,777 | B1 | 12/2001 | Sutter ...................... 433/173 | GB | 2 252 501 A | 8/1992 | |
| 6,461,160 | B1 * | 10/2002 | Sutter ...................... 433/173 | WO | WO 85/02337 | 6/1985 | |
| 6,488,501 | B1 * | 12/2002 | Harding .................. 433/173 | WO | WO 88 03007 | 5/1988 | |
| 6,655,962 | B1 | 12/2003 | Kennard | WO | WO 93 20774 | 10/1993 | |
| 6,663,388 | B1 | 12/2003 | Schar et al. | WO | WO 96/19946 | 7/1996 | |
| 6,726,480 | B1 | 4/2004 | Sutter | WO | WO 96/19947 | 7/1996 | |
| 6,974,322 | B2 | 12/2005 | May et al. | WO | WO 96/29019 | 9/1996 | |
| 6,981,873 | B2 | 1/2006 | Choi et al. | WO | WO 96/29020 | 9/1996 | |
| 2002/0106610 | A1 | 8/2002 | Hurson | WO | WO 97/01306 | 1/1997 | |
| 2004/0137406 | A1 | 7/2004 | Kennard | WO | WO 97/06930 | 2/1997 | |
| 2005/0181334 | A1 * | 8/2005 | Jacobs ...................... 433/215 | WO | WO 97/14371 | 4/1997 | |
| 2005/0202370 | A1 | 9/2005 | Brajnovic | WO | WO 97/20518 | 6/1997 | |
| 2005/0266382 | A1 * | 12/2005 | Soler et al. ............... 433/173 | WO | WO 97/27816 | 8/1997 | |
| 2006/0228672 | A1 | 10/2006 | Hurson | WO | WO 97/28755 | 8/1997 | |
| 2007/0190489 | A1 * | 8/2007 | Riley et al. ................ 433/173 | WO | WO 97/28756 | 8/1997 | |
| | | | | WO | WO 98/31296 | 7/1998 | |

FOREIGN PATENT DOCUMENTS

| | | | | | |
|---|---|---|---|---|---|
| | | | WO | WO 98/32393 | 7/1998 |
| DE | 12 32 314 | 1/1967 | WO | WO 98/36701 | 8/1998 |
| DE | 15 41 2 25 | 4/1970 | WO | WO 98/52490 | 11/1998 |
| DE | 2 114 323 | 10/1971 | WO | WO 99/04723 | 2/1999 |
| DE | 31 106 93 | 9/1982 | WO | WO 99/29255 | 6/1999 |
| DE | 31 10694 | 9/1982 | WO | WO 02/17814 | 3/2002 |
| DE | 35 31 389 A1 | 3/1987 | | | |

* cited by examiner

METHOD FOR FORMING A DENTAL PROSTHESIS

FIELD OF INVENTION

The present invention relates to a method of forming a dental prosthesis. More particularly, a method of forming a provisional as well as a permanent prosthesis to be applied to at least one or two dental implants is provided.

BACKGROUND OF THE INVENTION

The dental restoration of a partially or wholly endentulous patient with artificial dentition may be a lengthy process. Some patients undergo a two stage procedure, wherein the first stage entails implanting an implant in a bone for integration. A period of time is allowed for the patient to heal, and for the implant to osseointegrate with the bone. After this period of time, the second stage involves attaching prosthetic components to the implant. These prosthetic components may include healing components to allow gingival tissue to acquire a shape that mimics a natural gingival tissue shape, or the prosthetic components may include restoration components, such as, for example, an abutment and a crown.

Recently, some patients have been undergoing single-stage implant procedures in which a practitioner places an implant and attaches prosthetic components during the same office visit. Often times a pre-made provisional prosthesis will be placed on a patient while a permanent prosthesis is being developed. Many pre-made provisional prosthesis have a shape that is not specific to that patient, but the provisional prosthesis simply replicates a typical shape of a set of teeth. One drawback associated with such a pre-made provisional prosthesis is attaching a pre-made provisional prosthesis to the implant, as implants may not be placed exactly in a planned location, attaching locations on the pre-made provisional prosthesis may not align with the placed implants. Thus, alterations may be required to allow the pre-made provisional prosthesis to mount to the implants. Thus, a need exists for a method of forming a patient specific provisional dental prosthesis.

SUMMARY OF THE INVENTION

According to one process, a method of creating a provisional dental prosthesis on an implant placed in bone retains a conical abutment to the implant. A first intermediate component secures to the conical abutment. A second intermediate component attaches to the first intermediate component. The second intermediate component comprises a polymeric material. A prosthetic template is placed over the second intermediate component. The prosthetic template is filled with a hardenable material. After the prosthetic template is filled, the process removes the prosthetic template with the second intermediate component within the hardenable material. A provisional prosthesis forms from the hardenable material, the provisional prosthesis contains the second intermediate component. The provisional prosthesis connects to the first intermediate component by affixing the second intermediate component to the first intermediate component.

According to another process, a method of forming a dental prosthesis on a plurality of implants placed in bone attaches a conical abutment to each of the plurality of implants. A metallic first intermediate component is secured to each of the conical abutments. A polymeric second intermediate component is applied to each of the metallic first intermediate components via a snap-fit. The method places a provisional prosthetic template over the second intermediate components. The provisional prosthetic template forms an inner cavity that generally replicates shapes of teeth replaced by the provisional prosthesis. The provisional prosthetic template fills with a hardenable acrylic material. The method removes the provisional prosthetic template with the polymeric second intermediate components from the mouth. A provisional prosthesis forms from the hardenable acrylic material, the provisional prosthesis containing the polymeric second intermediate components. The provisional prosthesis connects to the metallic first intermediate components by placing the polymeric second intermediate components on the metallic first intermediate components. The method creates a permanent prosthesis. The provisional prosthesis and the metallic first intermediate components are removed after the creation of the permanent prosthesis. The permanent prosthesis attaches to the conical abutments.

According to a further process, a method forms a provisional dental prosthesis on a plurality of implants placed in bone. The implants have abutments attached thereto. The method includes securing a first intermediate component to each of the abutments. A polymeric second intermediate component attaches to each of the first intermediate components. A provisional prosthetic template is placed over the second intermediate components. The provisional prosthetic template forms an inner cavity that generally replicates the shape of the provisional prosthesis. The method fills the provisional prosthetic template with a hardenable acrylic material to form a provisional prosthesis. The provisional proshetic template is removed.

Figure 1:
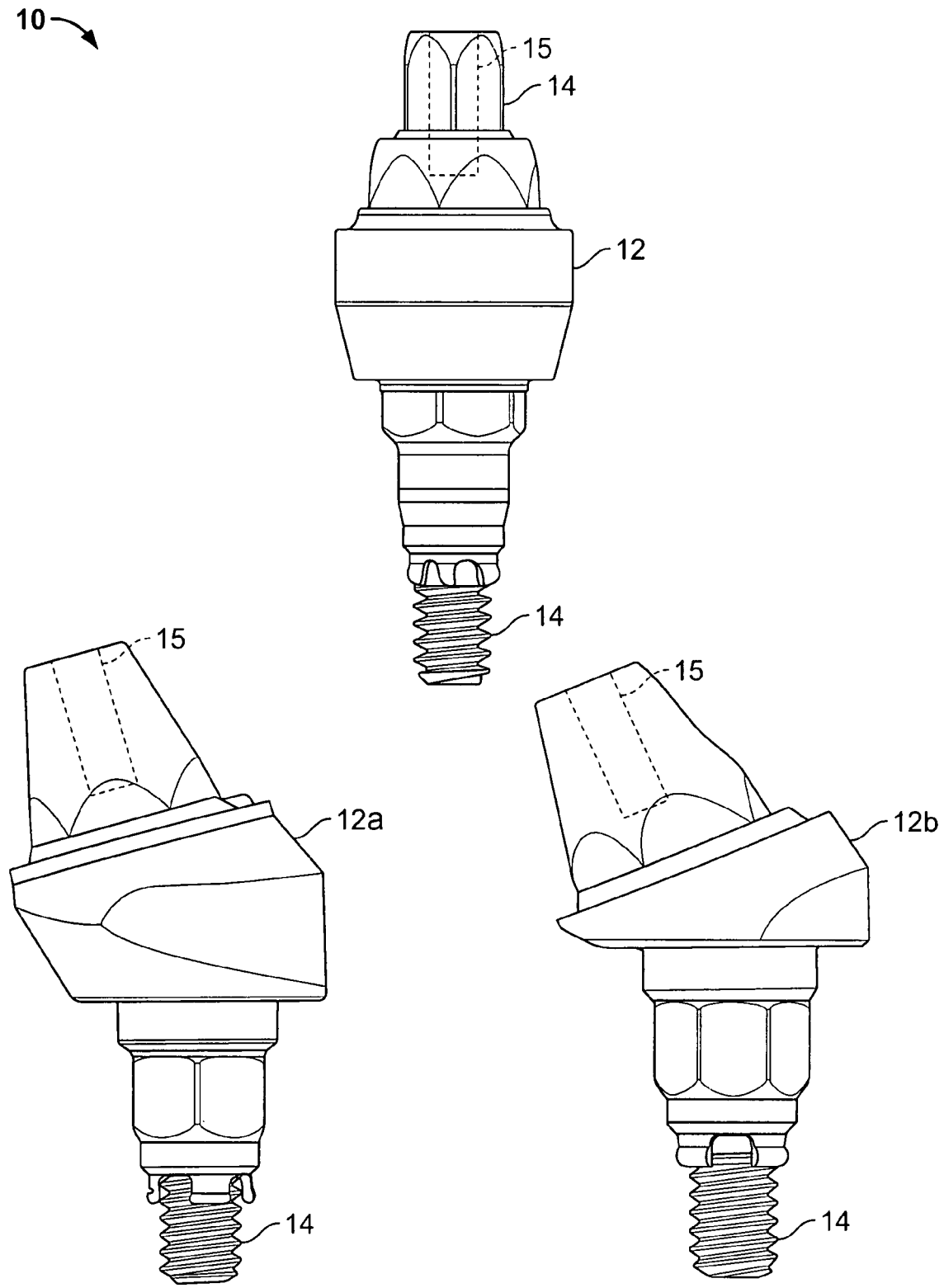
FIG. 1 includes side views of straight conical abutments and angled conical abutments for attachment to an implant.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

As shown in FIG. 1, a dental abutment assembly 10 comprises a dental abutment 12 and an abutment screw 14. The dental abutment assembly 10 is used with a dental implant (not shown) that is placed within bone of a patient. The abutment 12 shown in FIG. I is a conical type abutment. That is, the abutment 12 has a region with a generally conical shape. The abutment 12 is retained to the implant by the abutment screw 14 to form a dental implant assembly. The abutment 12 is connected to the implant after the implant is placed within the bone of the patient via the abutment screw 14. As will be described in more detail below, the abutment 12 or the abutment screw 14 includes a threaded bore 15 for retaining the intermediate components described below in FIG. 2.

While the conical abutment 12 illustrated in FIG. 1 is a generally straight conical abutment, it is contemplated that an angled conical abutment may be used. FIG. 1 also shows two conical abutments 12a and 12b having a known angle (e.g., 15° or 25°) relative to the central axis of the underlying implant. The head of the screw 14 in the angled abutments is positioned within a recess in the body of the abutment 12 and, therefore, is not shown.

Figure 2A:
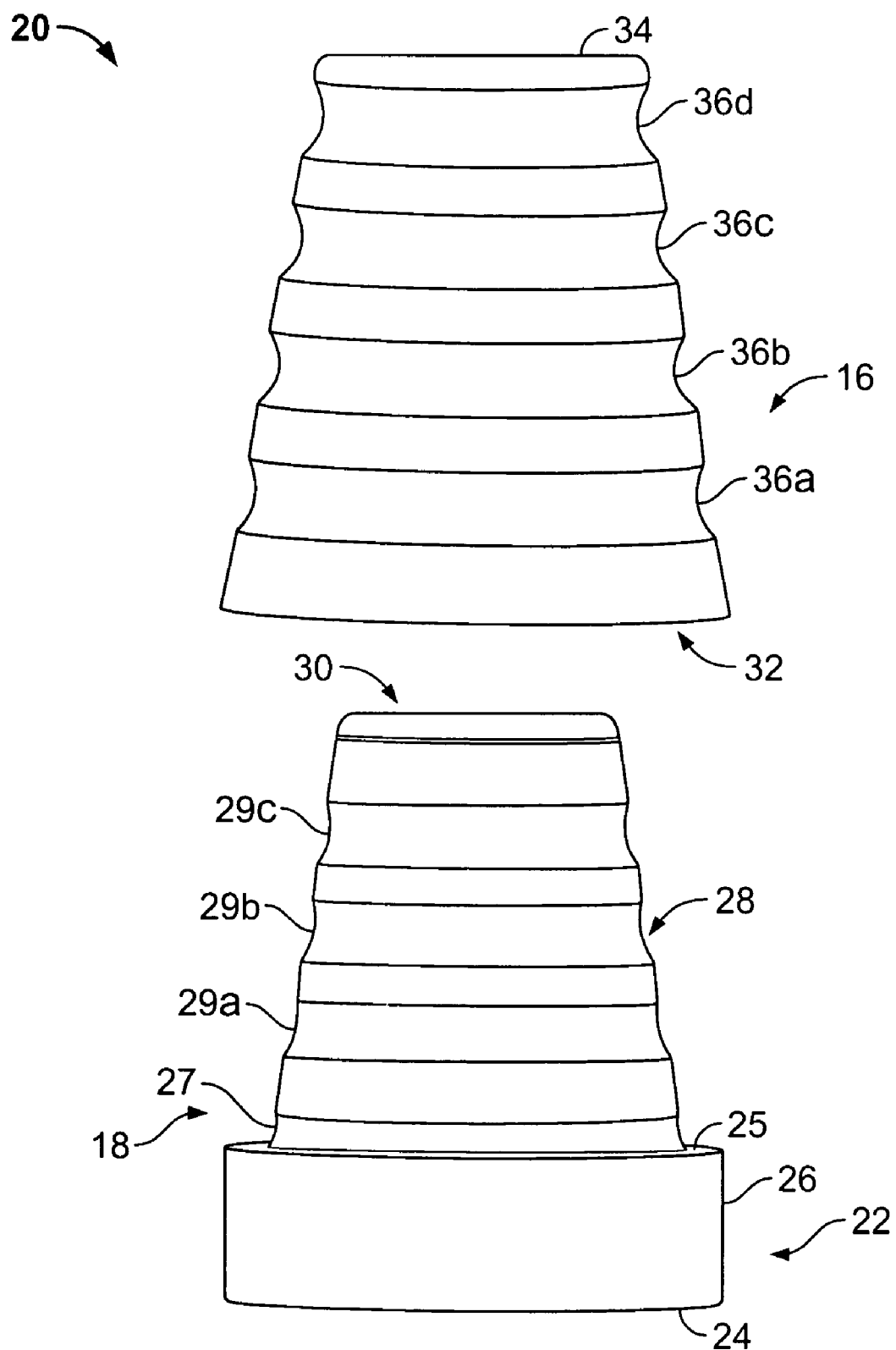
FIG. 2A is a front exploded view of a first intermediate component and a second intermediate component for use with the conical abutment of FIG. 1.
Figure 2B:
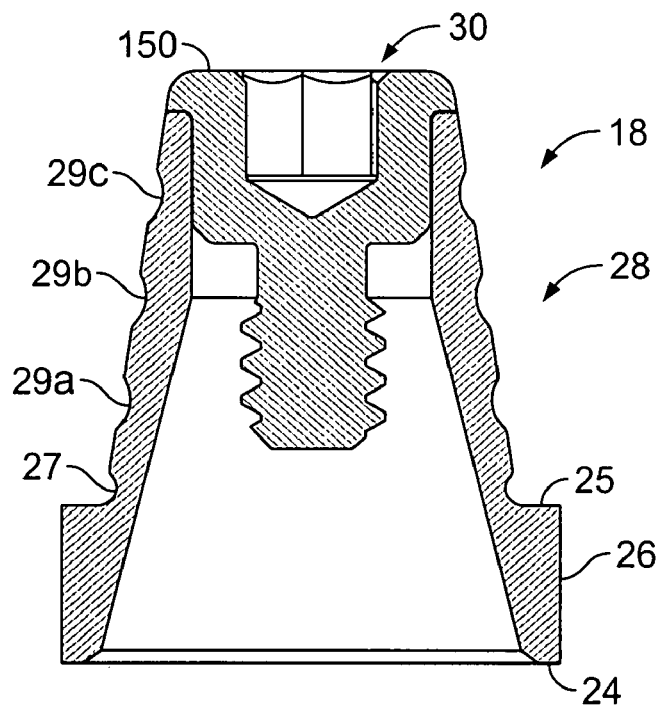
FIGS. 2B and 2C are side cross-sectional views of the first intermediate component and the second intermediate component of FIG. 2A.
Figure 2C:
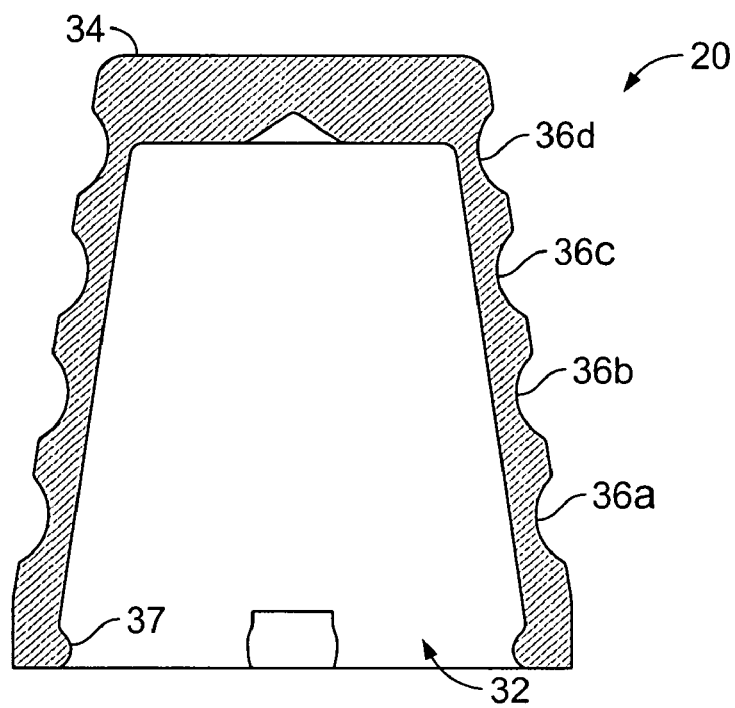

Turning next to FIGS. 2A, 2B, and 2C, a provisional component assembly 16 comprises a first intermediate component 18 and a second intermediate component 20. The first intermediate component 18 is generally hollow, allowing the first intermediate component 18 to be placed over the abutment 12 once the abutment 12 is mounted to the implant. The first intermediate component 18 has a connecting region 22 and a supporting region 28. The connecting region 22 has a bearing surface 24 adapted to contact the abutment 12. The connecting region 22 additionally has a shoulder surface 25. A sidewall 26 connects the support surface 24 to the shoulder surface 25. A retention groove 27 is located along the outer surface of the first intermediate component 18. As shown, the retention groove 27 is located directly above the shoulder surface 25.

The supporting region 28 of the first intermediate component 18 is adapted to support the second intermediate component 20. As shown in FIG. 2, it is contemplated that the supporting region 28 may have a plurality of ribs 29a-29c formed in a periphery of the supporting region 28 of the first intermediate component 18. The plurality of ribs 29a-29c generally do not extend into the hollow region of the first intermediate component 18.

It is contemplated that the first intermediate component 18 comprises a metallic material. According to one embodiment, the first intermediate component 18 comprises titanium. According to another embodiment, the first intermediate component 18 comprises a titanium alloy.

A top section 30 of the first intermediate component 18 is adapted to allow a screw 150 (FIG. 2B and FIG. 4) to pass through a portion of the internal through-bore to secure the first intermediate component 18 to the abutment 12. The threads of the screw 150 may attach to a threaded bore 15 in the abutment 12 or to a threaded bore 15 in a head of a screw holding the abutment 12 to the implant, which are shown in FIG. 1. The screw 150 used to retain the first intermediate component 18 to the abutment 12 may be press fit into the first intermediate component 18 prior to the practitioner placing the first intermediate component 18 in contact with the abutment 12. It is additionally contemplated that the first intermediate component 18 may have an integral screw section, thus, eliminating the need for a separate screw (e.g., screw 150) to secure the first intermediate component to the abutment 12.

The second intermediate component 20 has an internal bore 32 with a generally conical shape that is generally complimentary to the shape of the periphery of the first intermediate component 18. The generally complimentary shape of the internal bore 32 of the second intermediate component 20 allows the secondary intermediate component 20 to be placed over the first intermediate component 18.

The second intermediate component 20 is generally a cap to be placed over the first intermediate component 18. It is contemplated that the second intermediate component 20 and the first intermediate component 18 form a press-fit, or snap-fit, therebetween. In the illustrated embodiment, a retention structure 37 within the internal bore 32 of the second intermediate component 20 contacts the retention groove 27 of the first intermediate component 18 just above the shoulder surface 25. As such, the diameter of the internal bore 32 at the retention structure 37 is sized to form a snap-fit engagement with the retention groove 27.

As shown in FIG. 2, the second intermediate component 20 has a top surface 34. The top surface 34 is a continuous surface, preventing material from entering the cavity between the second intermediate component 20 and the first intermediate component 18.

The second intermediate component 20 may have a plurality of ribs 36a-36d formed in a periphery of the second intermediate component 20. The plurality of ribs 36a-36d generally do not extend into the internal bore 32 of the second intermediate component 20.

The second intermediate component 20 preferably comprises a polymeric material. One particular polymeric material well suited for use in the second intermediate component 20 is Polyetheretherketon ("PEEK"). However, it is contemplated that a variety of other non-metallic materials may be used in forming the second intermediate component 20. For example, the second intermediate component 20 could be made of multiple materials, such as a polymeric main piece with a metallic insert to create the retention structure 37 to fit within the retention groove 27 of the first intermediate component 18. Furthermore, the second intermediate component 20 may be metallic with a polymeric or elastomeric insert, such as an O-ring, to create the retention structure 37 to fit within the retention groove 27 of the first intermediate component 18.

Figure 3:
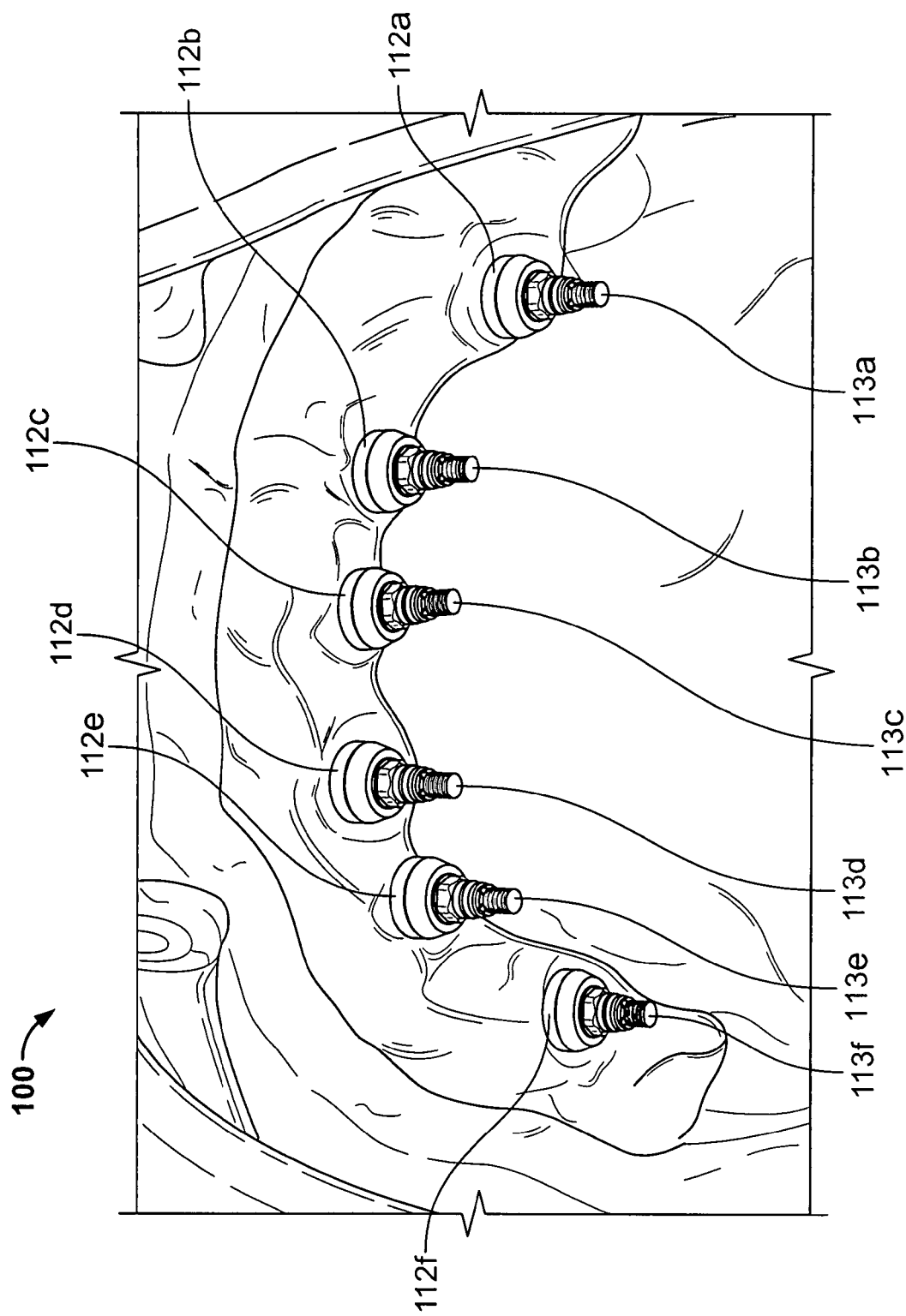
FIG. 3 is an isometric view of a patient's mouth with implants and conical abutments attached.

Turning next to FIGS. 3-8, a method of forming a provisional prosthesis will be described. As shown in FIG. 3, a patient's mouth 100 is shown containing a plurality of dental implants (not shown) having a plurality of abutments 112a-112f attached to the implants. The abutments 112a-112f are generally identical to the abutment 12 previously described relative to FIG. 1. The abutments 112a-112f are secured to the implants via a screw (not shown). The abutments 112a-112f each have a threaded section 113a-113f located at an end of the abutments 112a-112f opposite the implants. Once the abutments 112a-112f are attached to the implants, a plurality of first intermediate components 118a-118f may be attached.

Figure 4:
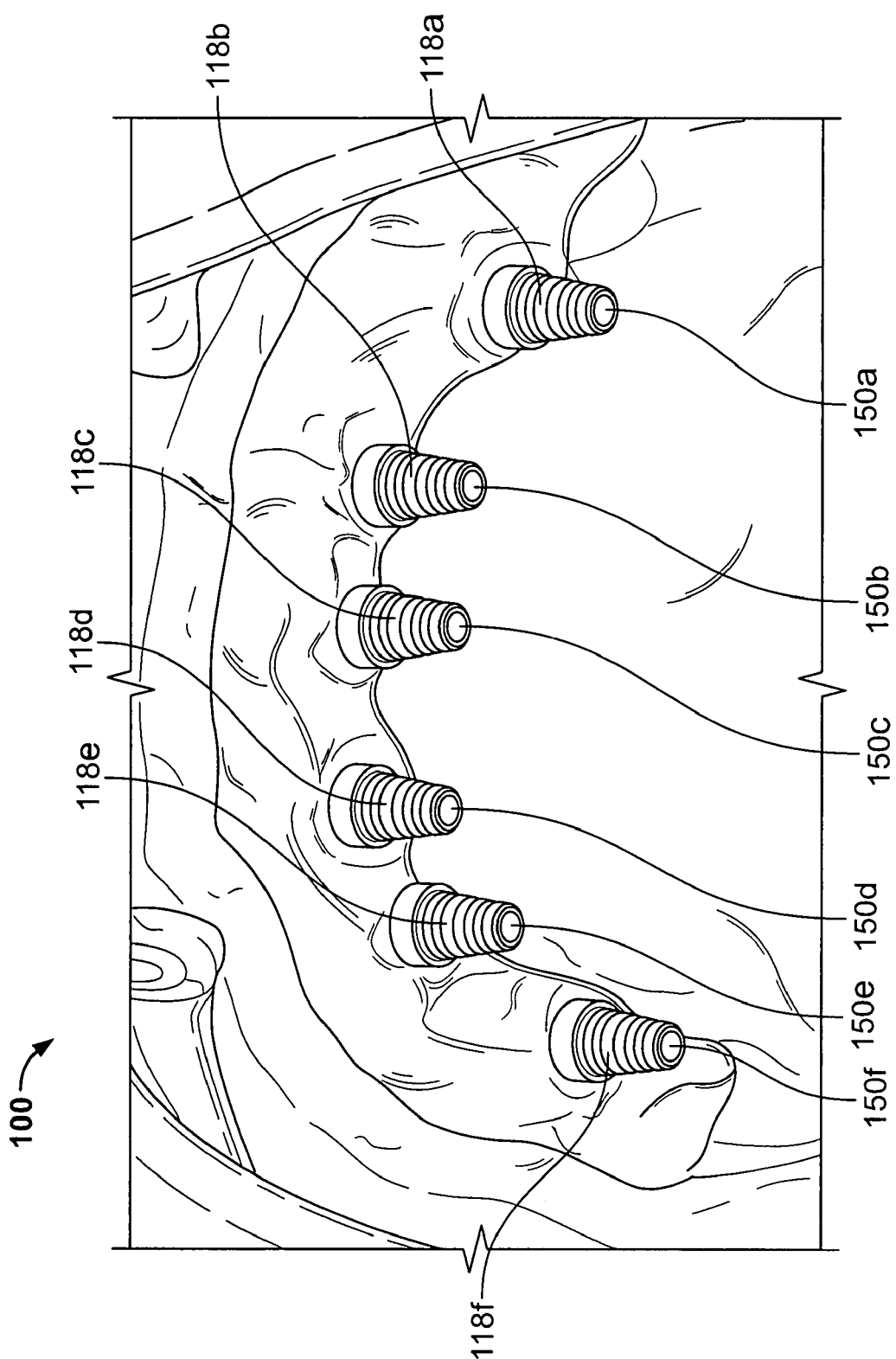
FIG. 4 is an isometric view of the patient's mouth of FIG. 3 with first intermediate components attached over the conical abutments.

FIG. 4 shows that the plurality of first intermediate components 118a-118f have been attached to each of the respective abutments 112a-112f. The first intermediate components 118a-118f are secured to the respective abutments 112a-112f via respective connecting screws 150a-150f. The connecting screws 150a-150f enter the first intermediate component at the top section 30 previously described in connection with FIG. 2. The screws 150a-150f interact with the threaded sections 113a-113f (FIG. 3) located at the end of the abutments 112a-112f opposite the implants.

Figure 5:
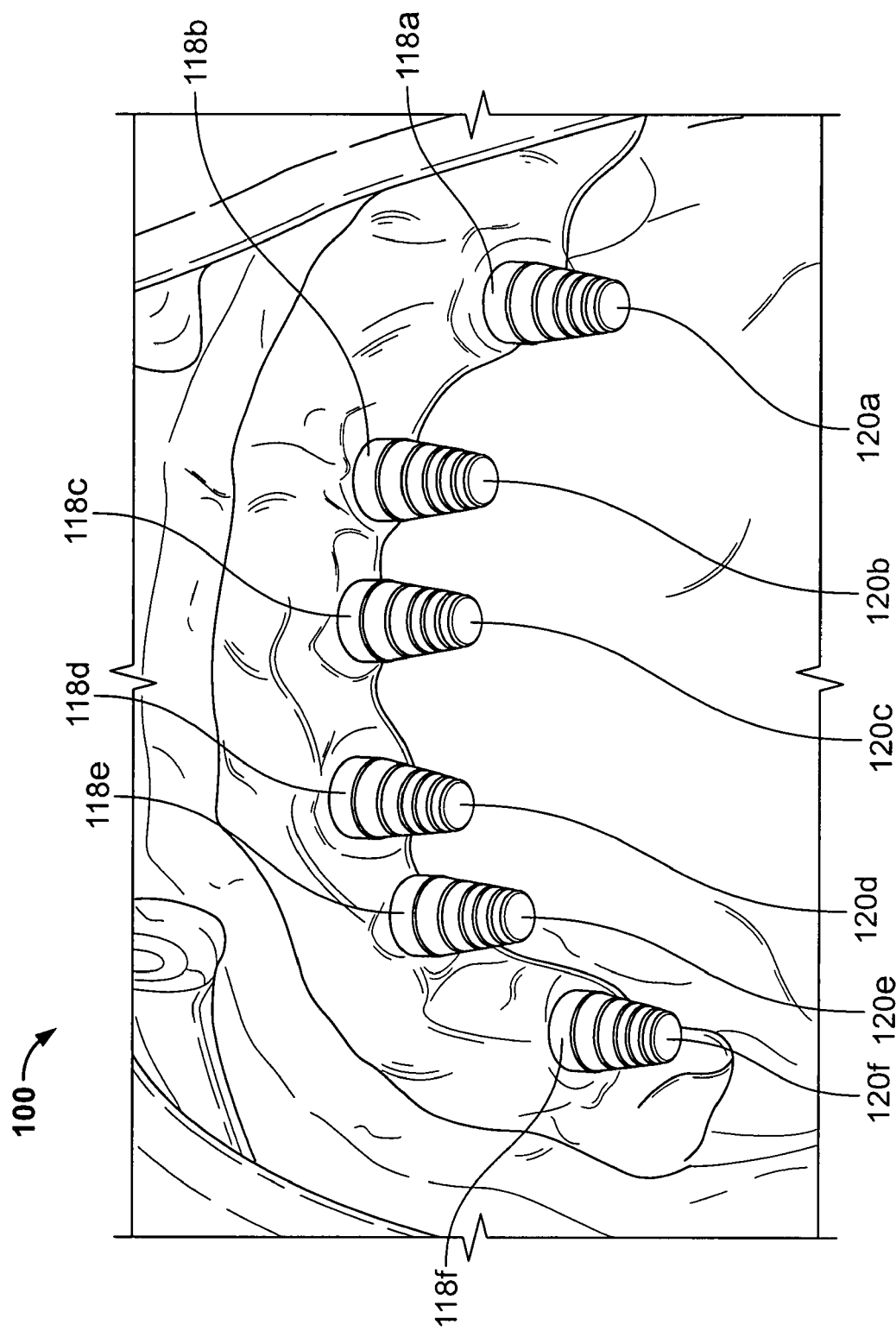
FIG. 5 is an isometric view of the patient's mouth of FIG. 4 with second intermediate components attached over the first intermediate components.

As shown in FIG. 5, a plurality of second intermediate components 120a-120f are placed over each of the plurality of first intermediate components 118a-118f. As previously described, the second intermediate components 120a-120f may initially be retained on the respective first intermediate components 118a-118f via a snap-fit. It is also contemplated that a press-fit may secure the second intermediate components 120a-120f to the first intermediate components.

Figure 6:
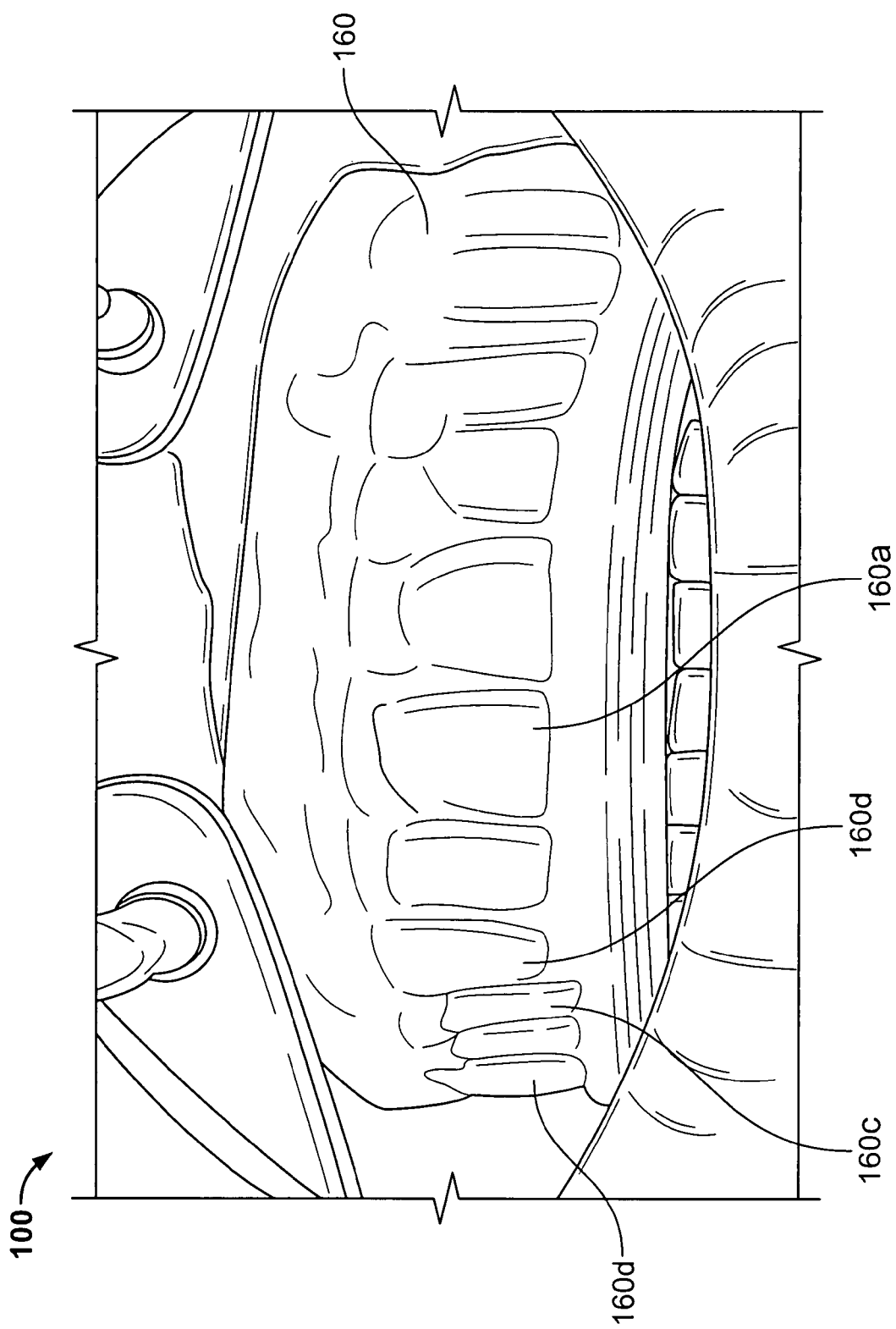
FIG. 6 is an isometric view of the patient's mouth of FIG. 5 with a prosthetic template placed over the second intermediate components.

After the second intermediate components 120a-120f are attached to the first intermediate components 118a-118f, a prosthetic template 160 is placed into the patient's mouth 100, as shown in FIG. 6. The prosthetic template 160 surrounds the second intermediate components 120a-120f. The prosthetic template 160 may contain a plurality of generally tooth shaped cavities, including tooth shaped cavities 160a-160d for each type of tooth in the patient. For example, generally tooth shaped cavity 160a corresponds to an incisor type tooth, generally tooth shaped cavity 160b corresponds to a canine type tooth, generally tooth shaped cavity 160c corresponds to a bicuspid type tooth, and generally tooth shaped cavity 160d corresponds to a molar type tooth. It is contemplated that a tooth shaped cavity for each tooth being replaced by the prosthesis is included in the prosthetic template 160.

The practitioner may have a number of prosthetic templates 160 to choose from. The various templates may vary in size and tooth shape to allow a practitioner to select a prosthetic template that provides an aesthetically pleasing provisional prosthesis for a particular patient.

The tooth shaped cavities of the prosthetic template 160 may be patient specific. For example, a stone model of the patient's mouth may be created in a dental laboratory that includes prosthetic teeth. An impression may be taken of the stone model. The impression will have generally the same shape as a prosthetic template. The prosthetic template may then be created from the impression. It is further contemplated that the prosthetic template may be made directly by taking an impression of the stone model of the patient's mouth.

It is additionally contemplated that the shape of the tooth shaped cavities of the prosthetic template may represent idealized shapes of teeth to be replaced within a patient. The idealized shapes of teeth representing a typical shape for a tooth located within a portion of the mouth containing the prosthesis.

Once the prosthetic template 160 is placed into the patient's mouth, the prosthetic template 160 is filled with a hardenable material. The hardenable material is typically a polymeric material. One example of a polymeric hardenable material suitable for use is acrylic. The hardenable material surrounds the second intermediate components 120a-120f. Ribs on second intermediate components, such as ribs 36a-36d shown in FIG. 2, allow the hardenable material to better capture the second intermediate components 120a-120f as the hardenable material hardens. Once the hardenable material has fully hardened, the prosthetic template 160 is removed from the patient's mouth. The removal of the prosthetic template 160 additionally removes the second intermediate components 120a-120f from the first intermediate components 118a-118f. The second intermediate components 120a-120f are secured within the hardenable material within the prosthetic template 160. The hardened material is removed from the prosthetic template 160, thus forming a provisional prosthesis 170.

Figure 7:
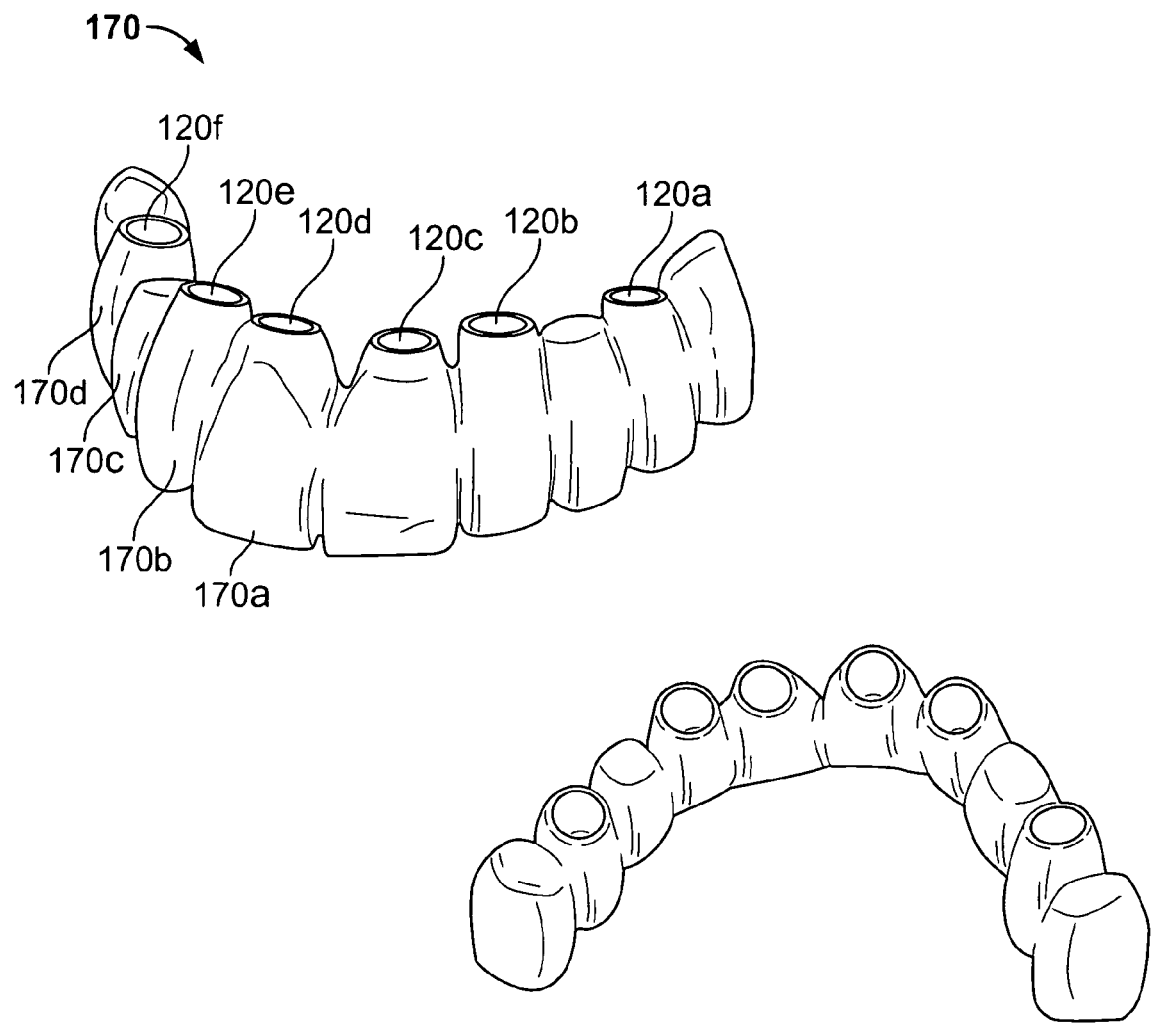
FIG. 7 is an isometric view of a provisional prosthesis created according to one method.

FIG. 7 shows a provisional prosthesis 170 formed within the prosthetic template 160. The provisional prosthesis contains the plurality of second intermediate components 120a-120f. The provisional prosthesis 170 may undergo additional processing steps prior to use in the patient, such as trimming and polishing, after being removed from the prosthetic template 160. The provisional prosthesis 170 has tooth shapes 170a-170d corresponding to the respective tooth shaped cavities 160a-160d found within the prosthetic template 160.

Once the provisional prosthesis 170 is fully prepared, it may be connected to the first intermediate components 118a-118f within the patient's mouth 100. The second intermediate components 120a-120f found within the provisional prosthesis 170 are placed over the first intermediate components 118a-118f still connected to the abutments 112a-112f connected to the plurality of implants within the patient's mouth 100. As the second intermediate components 120a-120f were removed from the first intermediate components 118a-118f after hardenable material was placed within the prosthetic template 160, alignment between the respective first intermediate components 118a-118f and the respective second intermediate components 120a-120f is precise.

The second intermediate components 120a-120f within the provisional prosthesis 170 may be secured to the first intermediate components 118a-118f via cement. Cement may be placed within ribs (e.g., 29a-29c FIG. 2) of the first intermediate components 118a-118f. The ribs allow the cement to fill the area between a bottom of the rib and a periphery of the first intermediate component. As the provisional prosthesis 170 is placed over the first intermediate components 118a-118f having cement within the ribs of the first intermediate components 118a-118f, the internal bore (e.g., 32 FIG. 2) of the second intermediate components 120a-120f contacts the cement, further securing the second intermediate components 120a-120f within the provisional prosthesis 170 to the first intermediate components 118a-118f attached to the abutments 112a-112f.

Similarly, it is contemplated that cement may be placed within the internal bore 32 of the second intermediate components 120a-120f, and as the provisional prosthesis 170 is placed over the first intermediate components 118a-118f, the cement spreads into the ribs (e.g., 29a-29c FIG. 2) of each of the first intermediate components 118a-118f.

It is further contemplated that a press-fit or a snap-fit may be utilized to secure the second intermediate components within the provisional prosthesis to the first intermediate components attached to the abutments within the patient's mouth.

Figure 8:
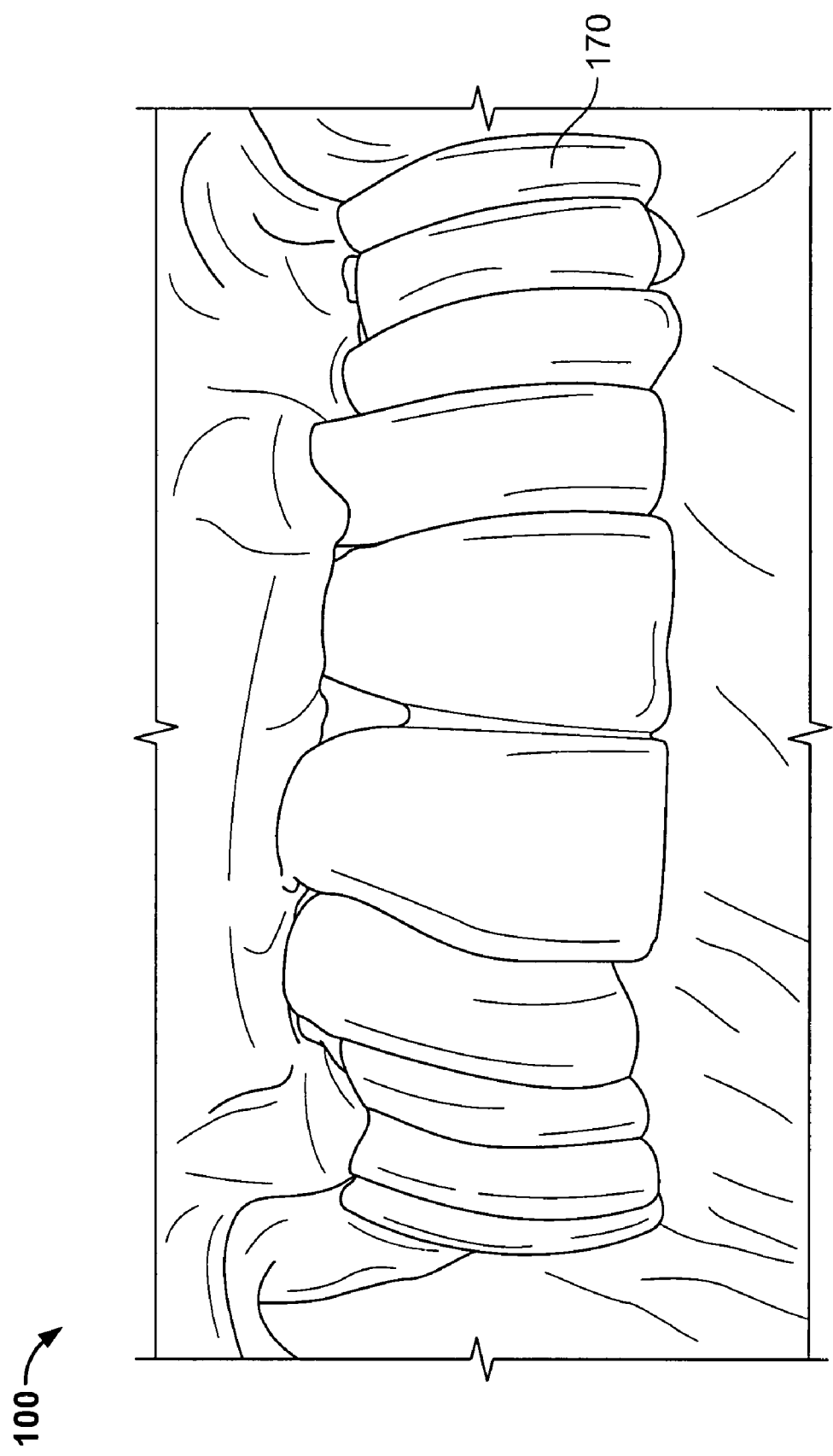
FIG. 8 is an isometric view of the patient's mouth with the provisional prosthesis attached.

As shown in FIG. 8, the provisional prosthesis 170 has been secured within the patient's mouth 100. The provisional prosthesis 170 remains in the patient's mouth 100 until a final permanent prosthesis may be created in a laboratory setting. The provisional prosthesis 170 allows a patient to have a cosmetically pleasing functional prosthesis soon after surgery, thus improving a patient's recovery.

Once the final permanent prosthesis is prepared, the provisional prosthesis 170 and the first intermediate components 118a-118f are removed from the patient's mouth. The final prosthesis is typically adapted to be retained directly to the conical abutments 112a-112f via fastening screws that connect into the threaded portions 113a-113f of the conical abutments 112a-112f. Thus, the first intermediate components 118a-118f and the second intermediate components 120a-120f allow the conical abutment 112 to be used to support a provisional prosthesis, and upon completion of a permanent prosthesis, the conical abutment 112 may be used to directly support the permanent prosthesis.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

The invention claimed is:

1. A method of creating a provisional dental prosthesis on an implant placed in bone comprising the acts of:
   retaining a conical abutment to the implant;
   securing a first intermediate component to the conical abutment;
   attaching a second intermediate component to the first intermediate component, the second intermediate component including a non-metallic material;
   placing a prosthetic template over the second intermediate component;
   filling the prosthetic template with a hardenable material;
   after the act of filling the prosthetic template, removing the prosthetic template with the second intermediate component within the hardenable material;
   forming a provisional prosthesis from the hardenable material, the provisional prosthesis containing the second intermediate component; and
   connecting the provisional prosthesis to the first intermediate component by affixing the second intermediate component to the first intermediate component.

2. The method of claim 1, wherein the first intermediate component comprises titanium.

3. The method of claim 1, wherein the act of securing the first intermediate component uses a screw to secure the first intermediate component to the conical abutment.

4. The method of claim 1, wherein the act of attaching the second intermediate component to the first intermediate component is a snap-fit.

5. The method of claim 1, wherein the hardenable material is acrylic.

6. The method of claim 1, wherein the prosthetic template has an inner cavity replicating a shape of teeth to be replaced by the prosthesis.

7. The method of claim 1, wherein the act of removing the prosthetic template occurs after waiting a period of time for the hardenable material to at least partially solidify.

8. The method of claim 1, wherein the act of connecting the provisional prosthesis to the first intermediate component includes placing cement between ribs of an outer periphery of the first intermediate component and the second intermediate component to secure the provisional prosthesis to the first intermediate component.

9. The method of claim 1, wherein the second intermediate component is made entirely of a polymeric material.

10. The method of claim 1 further comprising the acts of:
    removing the provisional prosthesis and the first intermediate component;
    attaching a permanent final prosthesis to the conical abutment.

11. A method of forming a dental prosthesis on a plurality of implants placed in bone comprising the acts of:
    attaching a conical abutment to each of the plurality of implants;
    securing a metallic first intermediate component to each of the conical abutments;
    applying a second intermediate component to each of the metallic first intermediate components via a snap-fit;
    placing a provisional prosthetic template over the second intermediate components, the provisional prosthetic template forming an inner cavity generally replicating shapes of teeth replaced by the provisional prosthesis;
    filling the provisional prosthetic template with a hardenable acrylic material;
    removing the provisional prosthetic template with the second intermediate components from the mouth;
    forming a provisional prosthesis from the hardenable acrylic material, the provisional prosthesis containing the second intermediate components;
    connecting the provisional prosthesis to the metallic first intermediate components by placing the second intermediate components on the metallic first intermediate components;
    creating a permanent prosthesis;
    removing the provisional prosthesis and the metallic first intermediate components after the act of creating a permanent prosthesis; and
    attaching the permanent prosthesis to the conical abutments.

12. The method of claim 11, wherein the metallic first intermediate component comprises titanium.

13. The method of claim 11, wherein the act of connecting the provisional prosthesis to the metallic first intermediate component includes placing cement between the metallic first intermediate component and the second intermediate component to secure the provisional prosthesis to the first intermediate component.

14. The method of claim 11, wherein at least one of the conical abutments is an angled abutment.

15. The method of claim 11, wherein the metallic first intermediate components have a generally conical shape.

16. The method of claim 15, wherein the metallic first intermediate components form a plurality of ribs about a periphery of the generally conical shape.

17. The method of claim 11, wherein the second intermediate components are polymeric and have a generally conical shape.

18. The method of claim 17, wherein the polymeric second intermediate components form a plurality of ribs about a periphery of the generally conical shape.

19. The method of claim 11, wherein the metallic first intermediate components have a generally conical shape and form a plurality of ribs about a periphery of the generally conical shape, the second intermediate components have a generally conical shape and form a plurality of ribs about a periphery of the generally conical shape.

20. The method of claim 19, wherein the act of connecting the provisional prosthesis to the metallic first intermediate component includes having cement within a gap between the plurality of ribs of the metallic first intermediate component and the second intermediate component to secure the provisional prosthesis to the first intermediate component.

21. The method of claim 11, wherein the provisional prosthetic template forming an inner cavity generally replicating shapes of teeth replaced by the provisional prosthesis is formed from a stone model of a patient.

22. The method of claim 11, wherein the provisional prosthetic template forming an inner cavity generally replicating shapes of teeth replaced by the provisional prosthesis is formed from a model of idealized teeth.

23. A method of forming a provisional dental prosthesis on a plurality of implants placed in bone, the implants having abutments attached, the method comprising the acts of:
    securing a first intermediate component to each of the abutments;
    attaching a second intermediate component to each of the first intermediate components, the second intermediate component including a non-metallic structure;

placing a provisional prosthetic template over the second intermediate components, the provisional prosthetic template forming an inner cavity generally replicating the shape of the provisional prosthesis;

filling the provisional prosthetic template with a hardenable acrylic material to form a provisional prosthesis;

removing the provisional prosthetic template.

24. The method of claim 23, wherein the first intermediate component comprises titanium.

25. The method of claim 23, wherein the act of securing the first intermediate component screws the first intermediate component to the abutment.

26. The method of claim 23, wherein the act of attaching the second intermediate component to the first intermediate component is a snap-fit.

27. The method of claim 23, wherein the act of attaching the second intermediate component to the first intermediate component is via cement.

28. The method of claim 23, wherein the second intermediate component comprises PEEK.

29. The method of claim 23, wherein the act of removing the provisional prosthetic template removes the second intermediate components from the first intermediate components allowing a practitioner to trim and polish the provisional prosthesis prior to use within the patient.

30. The method of claim 23, wherein the act of attaching the second intermediate component to the first intermediate component is via cement and the second intermediate components remain attached to the first intermediate components following the act of removing the prosthetic template resulting in the provisional prosthesis being mounted to the first intermediate components via the second intermediate components.

* * * * *